(12) United States Patent
Sakai (10) Patent No.: US 7,714,481 B2
(45) Date of Patent: May 11, 2010

(54) ULTRASONIC TREATMENT APPARATUS

(75) Inventor: Ryoji Sakai, Hachioji (JP)

(73) Assignee: Olympus Medical Systems Corp. (JP)

( * ) Notice: Subject to any disclaimer, the term of this patent is extended or adjusted under 35 U.S.C. 154(b) by 514 days.

(21) Appl. No.: 11/565,113

(22) Filed: Nov. 30, 2006

(65) Prior Publication Data
US 2008/0132927 A1    Jun. 5, 2008

(51) Int. Cl.
*H01L 41/08*    (2006.01)
(52) U.S. Cl. .............. 310/325; 310/323.01; 600/459; 604/22
(58) Field of Classification Search ........... 310/325, 310/334; 128/24 A, 305; 604/22, 272
See application file for complete search history.

(56) References Cited

U.S. PATENT DOCUMENTS

| | | | |
|---|---|---|---|
| 4,838,853 A | 6/1989 | Parisi | |
| 5,180,363 A | 1/1993 | Idemoto et al. | |
| 6,458,143 B1 | 10/2002 | Sugai | 606/169 |
| 2004/0087879 A1 | 5/2004 | Mitragotri et al. | |
| 2006/0241470 A1 | 10/2006 | Novak et al. | |
| 2006/0253050 A1 | 11/2006 | Yoshimine et al. | |

FOREIGN PATENT DOCUMENTS

| | | |
|---|---|---|
| EP | 0 908 154 | 4/1999 |
| JP | 2001 079013 | 3/2001 |

OTHER PUBLICATIONS

European Search Report dated Apr. 2, 2008 corresponding to European Patent Application No. 07018621.8.

*Primary Examiner*—Mark Budd
(74) *Attorney, Agent, or Firm*—Ostrolenk Faber LLP (57) ABSTRACT

An ultrasonic treatment apparatus includes an ultrasonic transducer that generates ultrasonic vibrations, a probe that includes a proximal end connected with the ultrasonic transducer, and transmits ultrasonic vibrations generated by the ultrasonic transducer from the proximal end to a distal end thereof, and a treatment portion that is formed at the distal end of the probe, and utilizes the transmitted ultrasonic vibrations to treat a living tissue. The treatment portion includes two or more protrusions.

15 Claims, 8 Drawing Sheets

ULTRASONIC TREATMENT APPARATUS

BACKGROUND OF THE INVENTION

1. Field of the Invention

The present invention relates to an ultrasonic treatment apparatus that utilizes ultrasonic vibrations to treat a living tissue.

2. Description of the Related Art

Various ultrasonic treatment apparatuses that utilize ultrasonic vibrations to treat a living tissue have been conventionally used.

A specification of U.S. Pat. No. 6,458,143 discloses an ultrasonic aspirator that emulsifies and fractures a living tissue and aspirates and removes the emulsified and fractured living tissue. In this ultrasonic aspirator, a hand piece grasped by an operator accommodates an ultrasonic transducer that generates ultrasonic vibrations therein. A proximal end of a probe is connected with this ultrasonic transducer, and this probe transmits ultrasonic vibrations generated by the ultrasonic transducer from the proximal end to a distal end thereof. A treatment portion that utilizes the transmitted ultrasonic vibrations to emulsify and fracture a living tissue is formed at the distal end of the probe. Further, an aspiration path extends in the probe along a central axis of the probe, and this aspiration path is opened at the distal end of the probe. The emulsified and fractured living tissue is aspirated and removed through this aspiration path. As a shape of the treatment portion of such a probe, a cylindrical shape whose inner bore forms the aspiration path is adopted.

BRIEF SUMMARY OF THE INVENTION

According to one aspect of the present invention, there is provided an ultrasonic treatment apparatus including: an ultrasonic transducer that generates ultrasonic vibrations; a probe that includes a proximal end connected with the ultrasonic transducer, and transmits ultrasonic vibrations generated by the ultrasonic transducer from the proximal end to a distal end thereof; and a treatment portion that is formed at the distal end of the probe and utilizes the transmitted ultrasonic vibrations to treat a living tissue, wherein the treatment portion includes two or more protrusions.

According to another aspect of the present invention, there is provided a probe for ultrasonic treatment apparatus that includes a proximal end connected with an ultrasonic transducer that generates ultrasonic vibrations, and transmits the ultrasonic vibrations generated by the ultrasonic transducer from the proximal end to a distal end thereof, the probe including a treatment portion that is formed at the distal end and utilizes the transmitted ultrasonic vibrations to treat a living tissue.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Each embodiment according to the present invention will now be described with reference to the accompanying drawings hereinafter.

Figure 1:
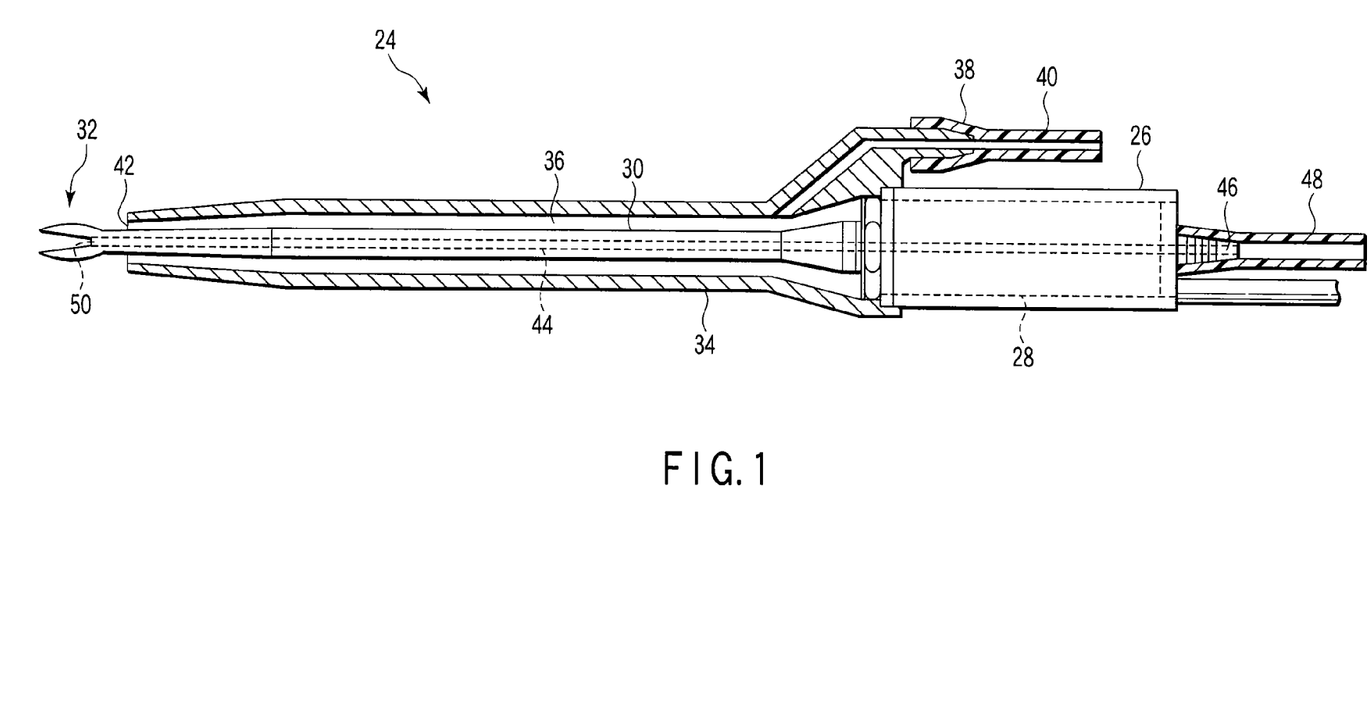
FIG. 1 is a longitudinal cross-sectional view showing an ultrasonic aspirator according to a first embodiment of the present invention.
Figure 2:
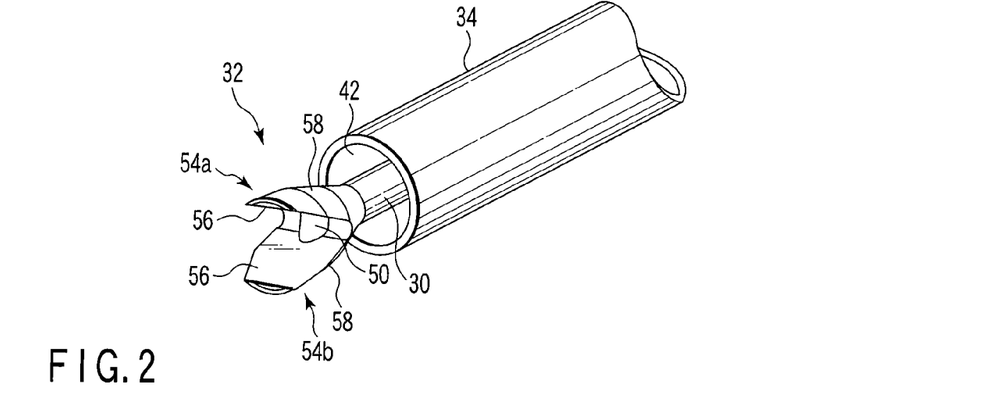
FIG. 2 is a perspective view showing a treatment portion according to the first embodiment of the present invention.
Figure 3:
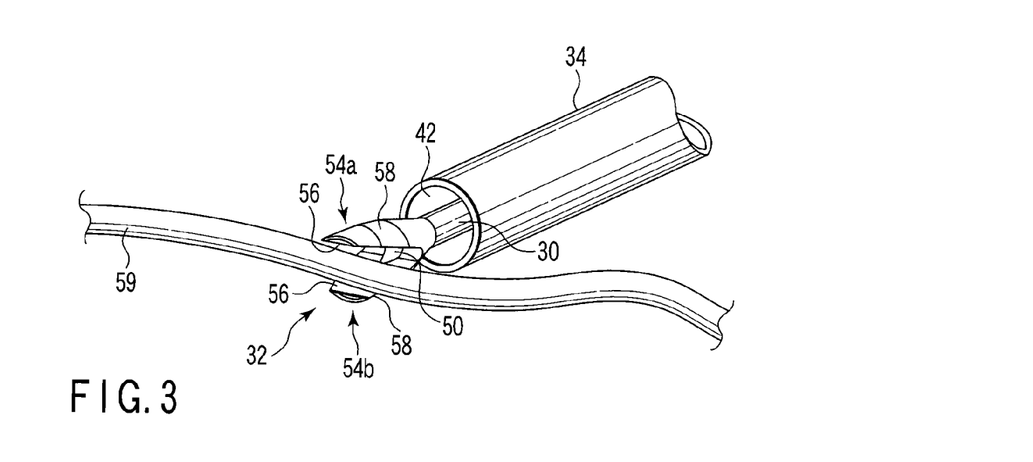
FIG. 3 is a perspective view showing a method for using the ultrasonic aspirator according to the first embodiment of the present invention.

FIGS. 1 to 3 show a first embodiment according to the present invention.

Referring to FIG. 1, an ultrasonic treatment apparatus according to this embodiment is an ultrasonic aspirator 24 that emulsifies and fractures a living tissue and aspirates and removes the emulsified and fractured living tissue.

This ultrasonic aspirator 24 has a hand piece 26 grasped by an operator. This hand piece 26 accommodates an ultrasonic transducer 28 that generates ultrasonic vibrations therein. A proximal end of a probe 30 is connected with an output end at a distal end of this ultrasonic transducer 28. This probe 30 transmits ultrasonic vibrations generated by the ultrasonic transducer 28 from the proximal end to a distal end thereof. A treatment portion 32 that utilizes the transmitted ultrasonic vibrations to treat a living tissue is formed at the distal end of the probe 30.

Furthermore, a proximal end of a sheath 34 is coupled with a distal end of the hand piece 26. This sheath 34 is provided on the probe 30, and the distal end of the probe 30 protrudes from a distal end of the sheath 34. Moreover, a tubular liquid supply path 36 is formed between an inner peripheral surface of the sheath 34 and an outer peripheral surface of the probe 30. A proximal end of this liquid supply path 36 communicates with a liquid supply connector 38 arranged at the proximal end of the sheath 34. This liquid supply connector 38 is connected with a liquid supply device through a liquid supply tube 40. On the other hand, a distal end of the liquid supply path 36 forms an annular liquid supply opening 42 at the distal end of the sheath 34. This liquid supply opening 42 is arranged near the rear side of the treatment portion 32 of the probe 30.

An aspiration path 44 extends in the probe 30 along a central axis of the probe 30. A proximal end of the aspiration path 44 of this probe 30 communicates with a aspiration connector 46 arranged at the proximal end of the hand piece 26 through an aspiration path formed in the ultrasonic transducer 28. This aspiration connector 46 is connected with the aspiration device through a aspiration tube 48. On the other hand, a distal end of the aspiration path 44 is opened at the treatment portion 32 to form a aspiration opening 50.

The treatment portion 32 according to this embodiment will now be explained in detail with reference to FIG. 2.

The treatment portion of the ultrasonic aspirator must have a small diameter to facilitate insertion into a body cavity, have a small size and a small weight to enable high-speed vibrations, and have sufficient strength so that it is not readily damaged by a repeated stress caused due to ultrasonic vibrations. Additionally, it is preferable in the treatment portion of the ultrasonic aspirator that cavitation is promoted. This cavitation occurs when the treatment portion ultrasonically vibrates in a liquid, e.g., humor, to reduce a pressure of a liquid near the treatment portion to a saturated vapor pressure or below of the liquid and promotes emulsification and fracture of a living tissue by the treatment portion.

The treatment portion 32 according to this embodiment maximizes a surface area of a part forming a shape with a large resistance coefficient that promotes cavitation while satisfying demands for small diameter, lightness, and high strength, and it is obtained as a result of sophisticated numerical analysis.

The treatment portion 32 according to this embodiment has a Y bill shape, and is formed of first and second protrusions 54a and 54b protruding toward the distal end side to be separated from the central axis of the probe 30. These first and second protrusions 54a and 54b are made up of inclined flat surface portions 56 facing each other, and gentle curved surface portions 58 on a rear surface side. The flat surface portion 56 has a shape having a large resistance coefficient. Therefore, when the treatment portion 32 is ultrasonically vibrated in a liquid, e.g., humor, a pressure gradient of the liquid becomes steep near the flat surface portion 56 and a decrease of the pressure is increased to readily reach a saturated vapor pressure. That is, the flat surface portion 56 promotes cavitation. It is to be noted that the aspiration opening 50 is arranged at a crotch portion of proximal ends of the first and second protrusions 54a and 54b.

A method for using the ultrasonic aspirator 24 according to this embodiment will now be explained.

In the following explanation, a technique of exposing a blood vessel buried in a fatty tissue will be taken as an example. This technique can be also applied to exposing a nerve buried in a fatty tissue.

The ultrasonic transducer 28 is driven to generate ultrasonic vibrations, and the probe 30 transmits the ultrasonic vibrations to ultrasonically vibrate the treatment portion 32, the ultrasonically vibrating treatment portion 32 is pressed against a fatty tissue covering a blood vessel as a treatment target to emulsify and fracture the fatty tissue. At this time, the liquid supply device supplies a normal saline solution to the treatment portion 32 and the fatty tissue from the liquid supply opening 42 through the liquid supply tube 40 and the liquid supply path 36 as required. As a result, the treatment portion 32 and the fatty tissue are immersed in a liquid containing, e.g., humor or the supplied normal saline solution. When the treatment portion 32 ultrasonically vibrates in the liquid, a pressure gradient of the liquid becomes steep near the flat surface portions 56 and a decrease of the pressure is increased so that the liquid reaches the saturated vapor pressure, whereby cavitation occurs. This cavitation promotes emulsification and fracture. The emulsified and fractured living tissue is aspirated from the aspiration opening 50 and removed through the aspiration path 44 and the aspiration tube 48 by the aspiration apparatus.

Referring to FIG. 3, when the blood vessel 59 as a treatment target is released from the fatty tissue, the separated blood vessel 59 is arranged between the first and second protrusions 54a and 54b to become perpendicular to a protruding direction of these protrusions 54a and 54b. Furthermore, the first and the second protrusions 54a and 54b are translated along an extending direction of the blood vessel 59 while being swiveled around the blood vessel 59. Since cavitation is promoted on the flat surface portions 56 of the first and the second protrusions 54a and 54b, cavitation is promoted near an outer periphery of the blood vessel 59, and the fatty tissue that has adhered to the outer periphery of the blood vessel 59 is efficiently emulsified, fractured, and removed. In this manner, the blood vessel 59 is completely exposed.

Incidentally, it is preferable to vibrate the treatment portion 32 at an antinode position of ultrasonic vibrations of the probe 30 at a vibration speed of 3.0 m/s or above in order to efficiently perform emulsification and fracture.

As explained above, in the ultrasonic aspirator 24 according to this embodiment, the two protrusions 54a and 54b form the treatment portion 32 to increase a surface area of a part forming a shape with a large resistance coefficient in the treatment portion 32, thereby promoting cavitation in the treatment portion 32. Therefore, the treatment portion 32 can efficiently emulsify and fracture the fatty tissue.

Furthermore, a blood vessel or a nerve is arranged between the two protrusions 54a and 54b to become perpendicular to the protruding direction of these protrusions 54a and 54b and the two protrusions 54a and 54b are translated along an extending direction of the blood vessel or the like while being swiveled around the blood vessel or the like, thereby efficiently emulsifying, fracturing, and removing a fatty tissue that has adhered to an outer periphery of the blood vessel or the like.

The treatment portion according to this embodiment aims at maximization of a surface area of a part forming a shape with a large resistance coefficient that promotes cavitation while satisfying demands for a small diameter, lightness, and high strength, and a shape and the number of the protrusions can be changed in many ways insofar as such an aim is fulfilled. Modifications in which the number of the protrusions is changed to three and four will be explained below.

Figure 4:
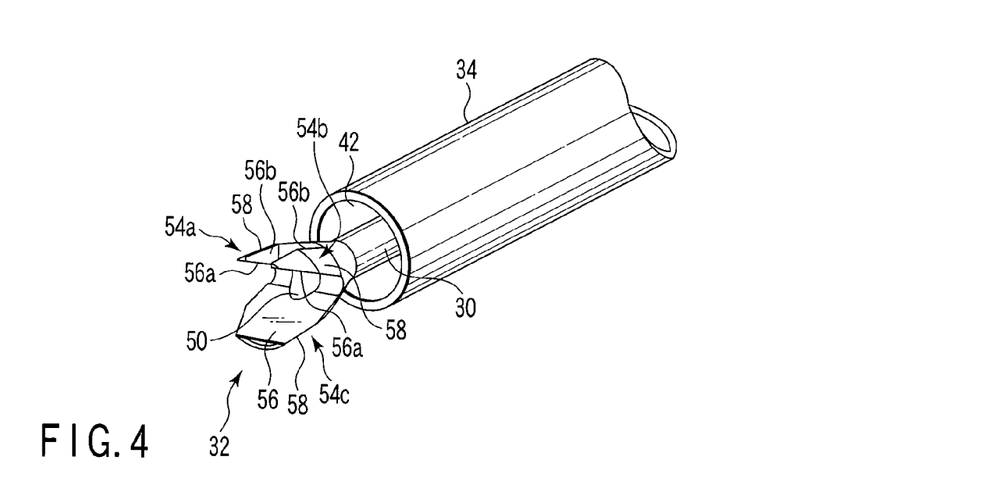
FIG. 4 is a perspective view showing a treatment portion according to a modification of the first embodiment of the present invention.
Figure 5:
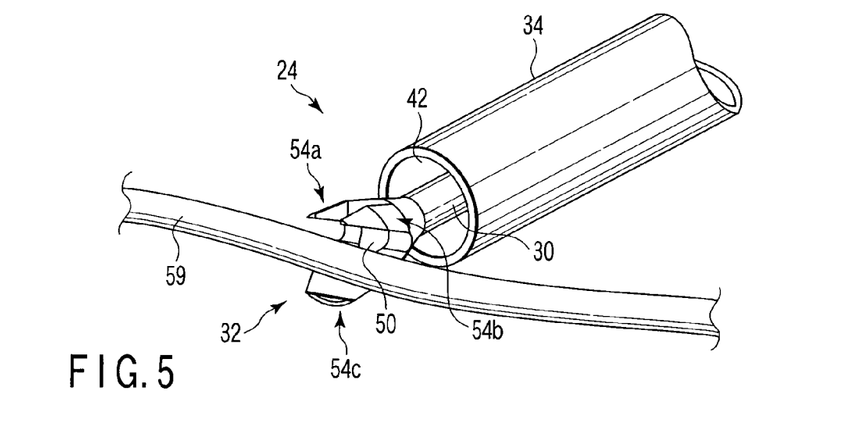
FIG. 5 is a perspective view showing a method for using an ultrasonic aspirator according to the first modification of the first embodiment of the present invention.

FIGS. 4 and 5 show a first modification of the first embodiment according to the present invention.

Referring to FIG. 4, the treatment portion 32 according to this modification is constituted of first to third protrusions 54a, 54b, and 54c. The first and the second protrusions 54a and 54b according to this modification have a shape obtained by notching the center of the first protrusion 54a according to the first embodiment shown in FIG. 2 along a central axis direction of the probe 30. The first and the second protrusions 54a and 54b are respectively formed of inclined first flat surface portions 56a facing the third protrusion 54c, second flat surface portions 56b facing each other, and gentle curved surface portions 58 on a rear surface side. A shape of each of the first and the second flat surface portions 56a and 56b is a shape with a large resistance coefficient, and the first and the second flat surface portions 56a and 56b promote cavitation. Moreover, the third protrusion 54c according to this modification has the same shape as that of the second protrusion 54b according to the first embodiment shown in FIG. 2.

As depicted in FIG. 5, a method for using the ultrasonic aspirator 24 according to this modification is the same as that in the first embodiment.

In this modification, forming the treatment portion 32 of the three protrusions 54a, 54b, and 54c further increases a surface area of a part forming a shape with a large resistance coefficient in the treatment portion 32 as compared with the example where the treatment portion is formed of the two protrusions 54a and 54b, thereby further promoting cavitation in the treatment portion 32.

Figure 6:
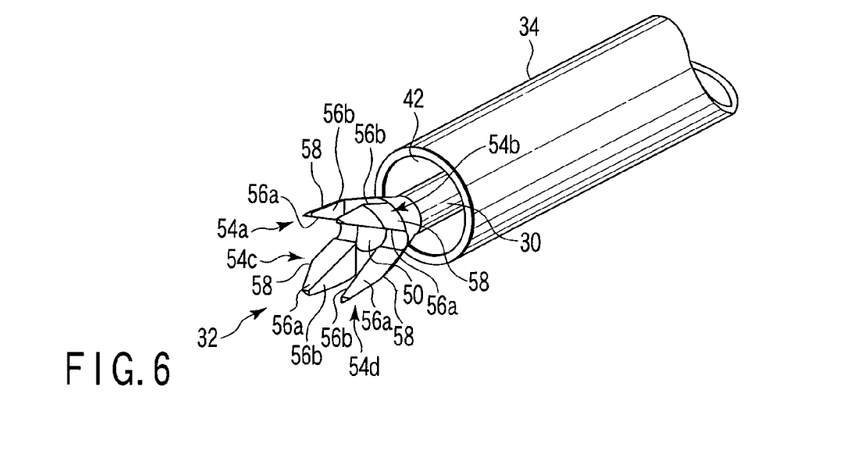
FIG. 6 is a perspective view showing a treatment portion according to a second modification of the first embodiment of the present invention.
Figure 7:
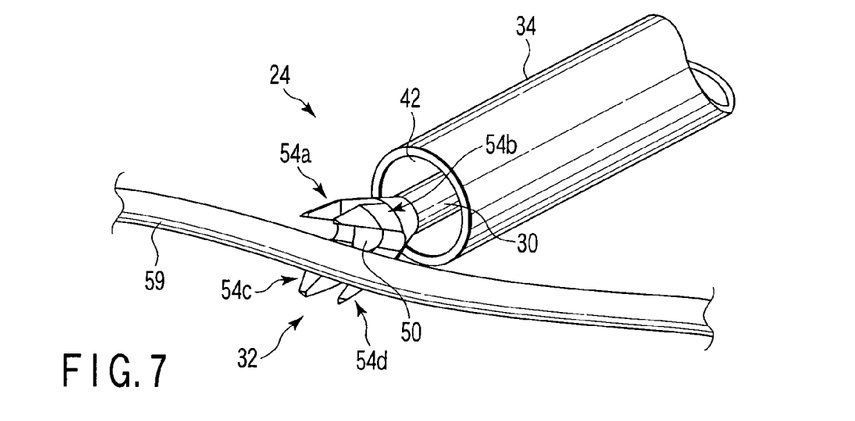
FIG. 7 is a perspective view showing a method for using an ultrasonic aspirator according to the second modification of the first embodiment of the present invention.

FIGS. 6 and 7 show a second modification of the first embodiment according to the present invention.

Referring to FIG. 6, the treatment portion 32 according to this modification is formed of first to fourth protrusions 54a, 54b, 54c, and 54d. The first and the second protrusions 54a and 54b according to this modification have the same shapes as those of the first and the second protrusions 54a and 54b according to the first modification. The third and the fourth protrusions 54c and 54d according to this modification have a shape obtained by notching the center of the third protrusion 54c according to the first modification depicted in FIG. 4 along the central axis direction of the probe 30. The first to the fourth protrusions 54a, 54b, 54c, and 54d have the first and second flat surface portions 56a and 56b and curved surface portions 58 like those in the first modification, and the first and the second flat surface portions 56a and 56b promote cavitation.

As shown in FIG. 7, a method for using the ultrasonic aspirator 24 according to this modification is the same as that in the first embodiment.

In this modifications, forming the treatment portion 32 of the four protrusions 54a, 54b, 54c, and 54d further increases a surface area of a part forming a shape with a large resistance coefficient in the treatment portion 32 as compared with the example in which the treatment portion is formed of the three protrusions 54a, 54b, and 54c, thereby further facilitating cavitation in the treatment portion 32.

Figure 8:
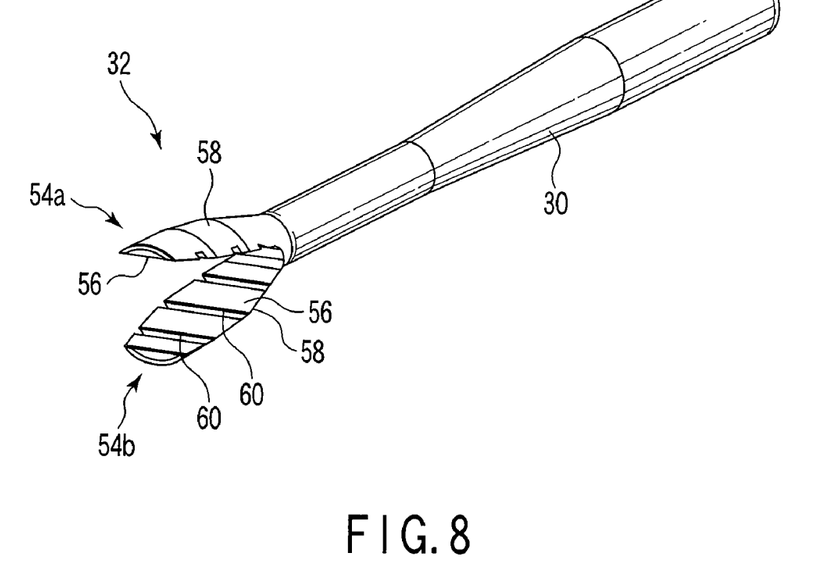
FIG. 8 is a perspective view showing a treatment portion according to a second embodiment of the present invention.

FIG. 8 shows a second embodiment according to the present invention.

In the treatment portion 32 according to this embodiment, promoting portions that promote cavitation are formed in each of the protrusions 54a and 54b. That is, a plurality of groove-like concave portions 60 extending in a width direction of each of the protrusions 54a and 54b are formed on the flat surface portions 56 of the first and the second protrusions 54a and 54b to be separated from each other with respect to a longitudinal direction of each of the protrusions 54a and 54b. These concave portions 60 further increase a resistance coefficient of each flat surface portion 56, thereby further promoting cavitation by each flat surface portion 56.

Figure 9:
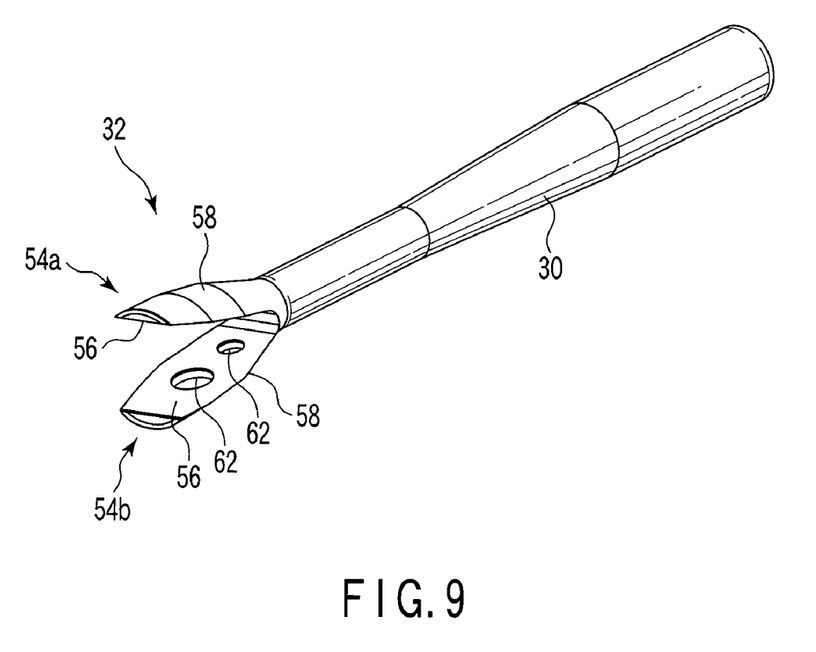
FIG. 9 is a perspective view showing a treatment portion according to a modification of the second embodiment of the present invention.

FIG. 9 shows a first modification of the second embodiment according to the present invention.

In this modification, a plurality of hole portions 62 as promoting portions piercing from the flat surface portion 56 to the curved surface portion 58 are formed in a second protrusion 54b. These hole portions 62 further increase a resistance coefficient of each of the flat surface portion 56 and the curved surface portion 58, cavitation by the flat surface portion 56 is further promoted, and cavitation is also promoted by the curved surface portion 58.

FIGS. 10 to 13 show a third embodiment according to the present invention.

Figure 10:
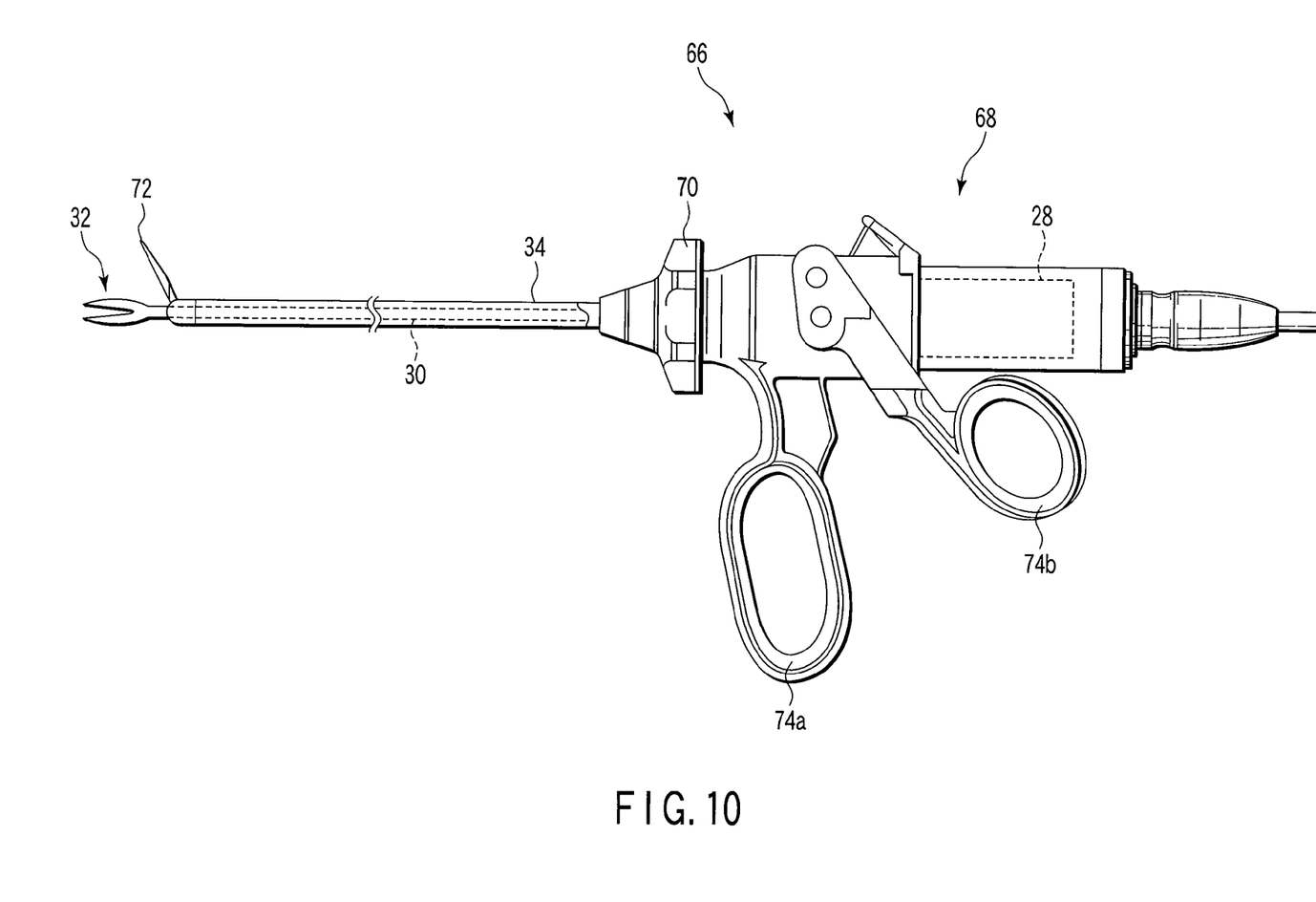
FIG. 10 is a side view showing an ultrasonic coagulation-cutting device according to a third embodiment of the present invention.

An ultrasonic treatment apparatus according to this embodiment is an ultrasonic coagulation-cutting device 66 that performs coagulation and cutting with respect to a living tissue.

This ultrasonic coagulation-cutting device 66 has an operating portion 68 operated by an operator. This operating portion 68 accommodates the ultrasonic transducer 28 therein. The same probe 30 as that in the first embodiment is connected with this ultrasonic transducer 28. A proximal end of the sheath 34 provided on this probe 30 is connected with a distal end of the operating portion 68. Additionally, a rotary knob 70 is arranged in the operating portion 68, and the sheath 34 can rotate around a central axis thereof when this rotary knob 70 is rotated. A jaw 72 that is opened and closed with respect to the treatment portion 32 and holds a living tissue in cooperation with the treatment portion 32 is arranged at a distal end of the sheath 34. This jaw 72 can be opened and closed by opening and closing a pair of handles 74a and 74b arranged in the operating portion 68.

Figure 11:
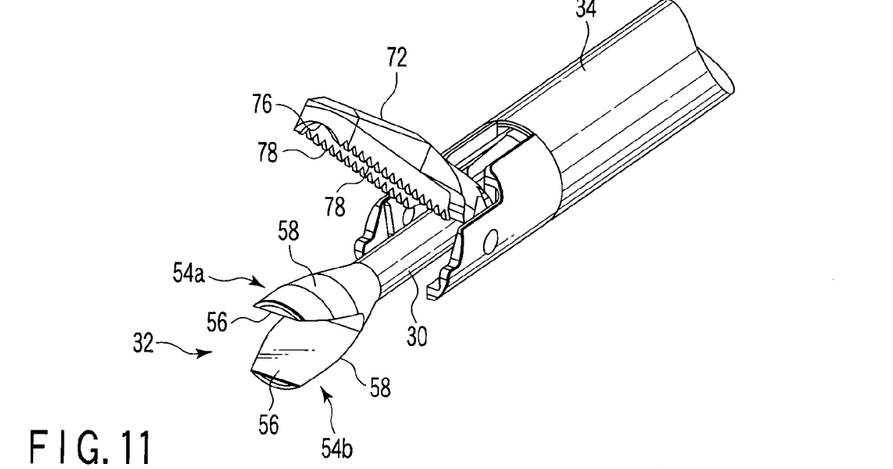
FIG. 11 is a perspective view showing a treatment portion according to the third embodiment of the present invention.

Referring to FIG. 11, the treatment portion 32 according to this embodiment has the same shape as that of the treatment portion 32 according to the first embodiment. The jaw 72 is provided pivotally at the distal end of the sheath 34 to swivel with respect to this treatment portion 32. A fitting groove 76 that can fit on a curved surface portion 58 of a first protrusion 54a of the treatment portion 32 is provided in this jaw 72 on the probe 30 side to be extended along a longitudinal direction of the jaw 72. Further, tooth portions 78 that avoid slippage of a living tissue are provided on both sides of the jaw 72 to be extended along the longitudinal direction of the jaw 72.

A method for using the ultrasonic coagulation-cutting device 66 according to this embodiment will now be explained.

In the following explanation, a technique of exposing a blood vessel buried in a fatty tissue and performing coagulation and cutting with respect to the exposed blood vessel will be taken as an example.

Figure 12:
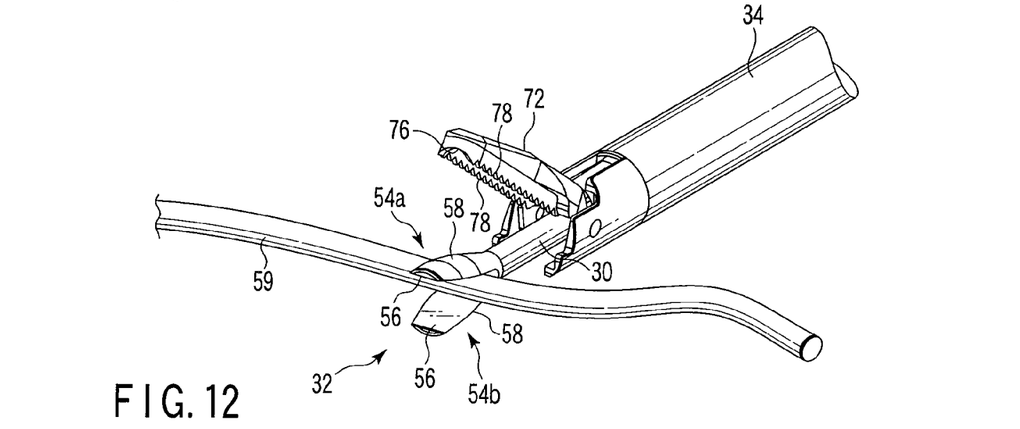
FIG. 12 is a perspective view showing removal of a fatty tissue from a blood vessel in a method for using the ultrasonic coagulation-cutting device according to the third embodiment of the present invention.

Referring to FIG. 12, a procedure from the beginning to exposing a blood vessel 59 buried in a fatty tissue is the same as that in the first embodiment.

Figure 13:
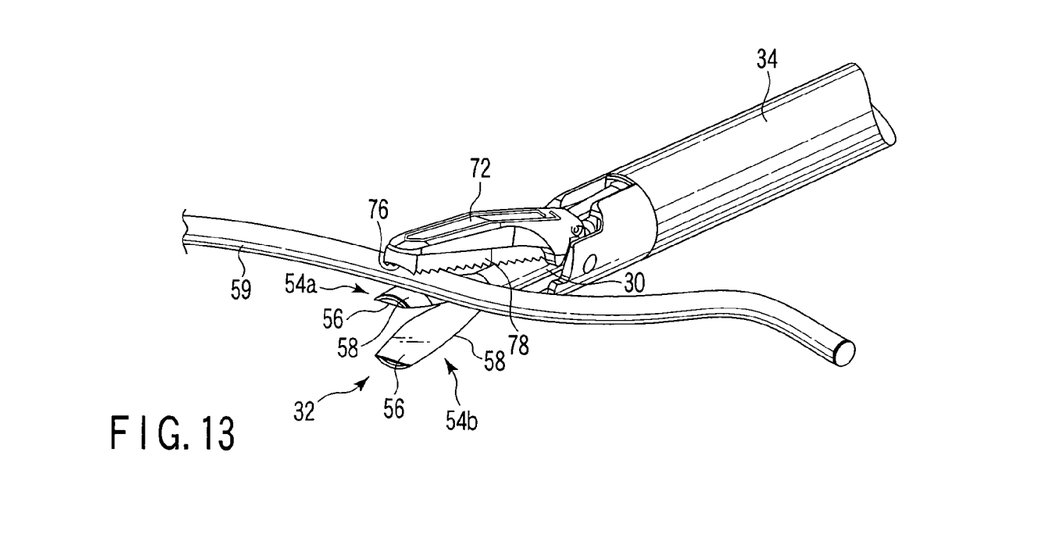
FIG. 13 is a perspective view showing coagulation and cutting of the blood vessel in the method for using the ultrasonic coagulation-cutting device according to the third embodiment of the present invention.

Referring to FIG. 13, the exposed blood vessel 59 is arranged between the first protrusion 54a and the jaw 72 to become perpendicular to the first protrusion 54a and the jaw 72. Subsequently, the pair of handles 74a and 74b in the operating portion 68 is closed to close the jaw 72 with respect to the first protrusion 54a, whereby the curved surface portion 58 of the first protrusion 54a on the rear surface side and the fitting groove 76 of the jaw 72 on the probe 30 side hold the blood vessel 59 therebetween. Furthermore, the treatment portion 32 is ultrasonically vibrated to perform coagulation and cutting with respect to the held blood vessel 59. It is to be noted that the coagulation and cutting is not necessarily promoted by cavitation, and the sufficient coagulation and cutting can be likewise carried out by utilizing the curved surface portion 58 rather than the flat surface portion 56 that promotes cavitation.

As explained above, in the ultrasonic coagulation-cutting device 66 according to this embodiment, like the first embodiment, the treatment portion 32 can efficiently emulsify and fracture a fatty tissue, and the treatment portion 32 and the jaw 72 can perform coagulation and cutting with respect to a blood vessel. That is, the ultrasonic coagulation-cutting device 66 according to this embodiment alone can expose a blood vessel buried in a fatty tissue and perform coagulation and cutting with respect to the exposed blood vessel, and hence the technique can be smoothly carried out with less invasion as compared with an example where a plurality of treatment instruments are inserted/removed.

Figure 14:
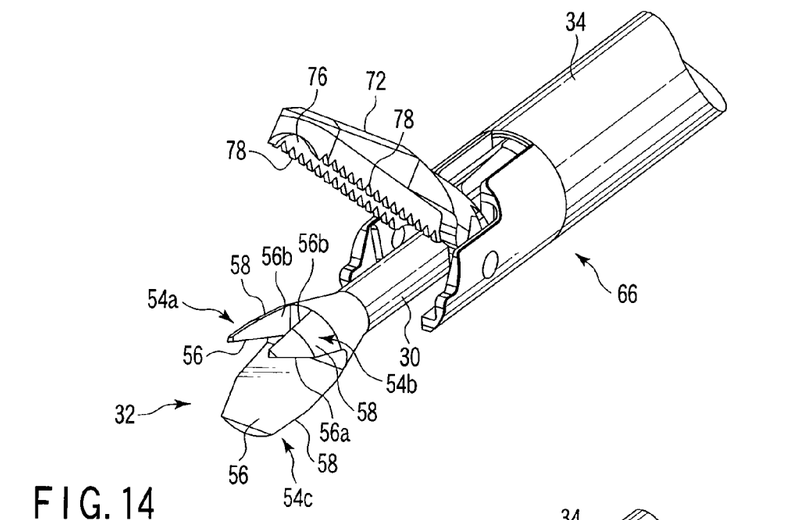
FIG. 14 is a perspective view showing a treatment portion according to a first modification of the third embodiment of the present invention.

FIG. 14 shows a first modification of the third embodiment according to the present invention.

The treatment portion 32 according to this modification has the same shape as that of the treatment portion 32 according to the first modification of the first embodiment depicted in FIG. 4. That is, cavitation in the treatment portion 32 is further promoted as compared with the treatment portion 32 according to the third embodiment. A method for using the ultrasonic coagulation-cutting device 66 according to this modification is the same as the method for using the ultrasonic coagulation-cutting device 66 according to the third embodiment depicted in FIG. 10. It is to be noted that, when holding a blood vessel between the treatment portion 32 and the jaw 72, the rotary knob 70 in the operating portion 68 is rotated to turn the sheath 34 and the jaw 72 around a central axis of the probe 30, the jaw 72 is arranged with respect to the treatment portion 32 at an appropriate position corresponding to a shape of the treatment portion 32 where holding can be facilitated, and then the blood vessel is held between these members.

Figures 15, 16:
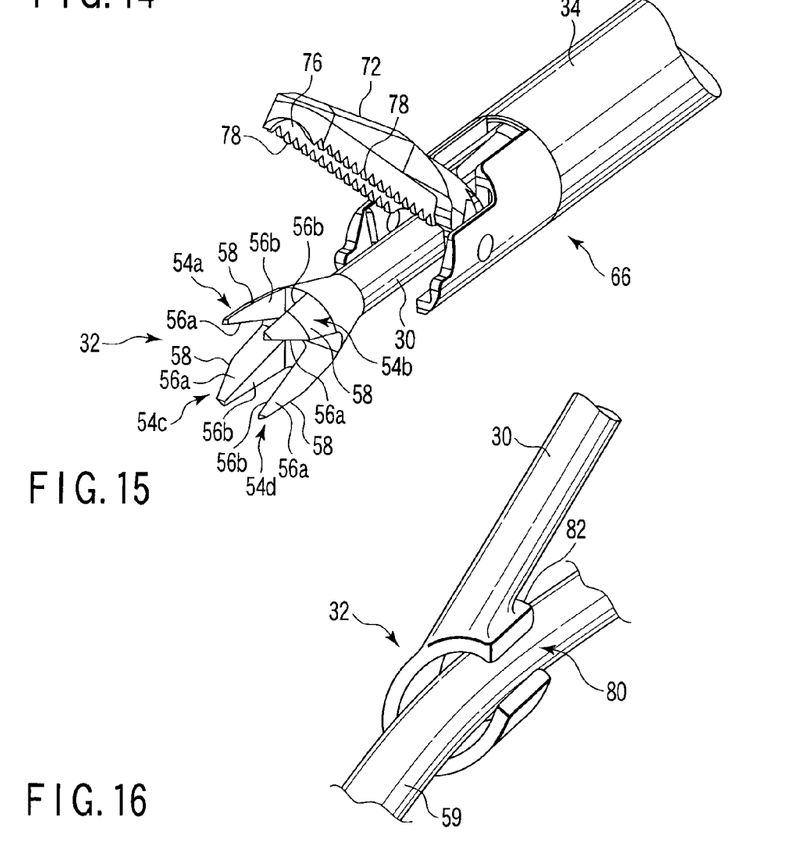
FIG. 15 is a perspective view showing a treatment portion according to a second modification of the third embodiment of the present invention.
FIG. 16 is a perspective view showing a treatment portion according to a first reference embodiment of the present invention.

FIG. 15 shows a second modification of the third embodiment according to the present invention.

A treatment portion 32 according to this modification has the same shape as that of the treatment portion 32 according to the second modification of the first embodiment depicted in FIG. 6. That is, cavitation in the treatment portion 32 is further promoted as compared with the treatment portion 32 according to the first modification of the third embodiment depicted in FIG. 14. A method for using the ultrasonic coagulation-cutting device 66 according to this modification is the same as a method for using the ultrasonic coagulation-cutting device 66 according to the first modification of the third embodiment depicted in FIG. 14.

Each reference embodiment serving as a useful reference of the present invention will now be explained.

Figure 17:
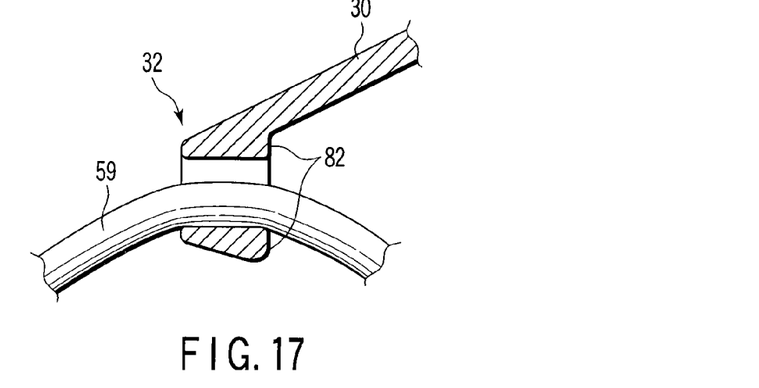
FIG. 17 is a longitudinal cross-sectional view showing the treatment portion according to the first reference embodiment of the present invention.

FIGS. 16 and 17 show a first reference embodiment according to the present invention.

Referring to FIG. 16, a treatment portion 32 of an ultrasonic treatment apparatus according to this reference embodiment has a shape where, in a circular cone whose apex side is a distal end side, an inner bore is formed along a central axis thereof and a notch portion 80 is formed entirely in an axial direction on an outer periphery portion thereof. That is, a lateral cross section of the treatment portion 32 vertical to the central axis forms a substantially-C-like shape. A proximal end surface 82 of the treatment portion 32 has a shape with a large resistance coefficient, and cavitation is facilitated on this proximal end surface 82.

Referring to FIGS. 16 and 17, when using the ultrasonic treatment apparatus according to this reference embodiment to remove a fatty tissue that has adhered to an outer periphery of a blood vessel 59, the blood vessel 59 released from the fatty tissue is led into the inner bore of the treatment portion 32 via the notch portion 80. Moreover, the treatment portion 32 is moved forward/backward along the blood vessel 59 while being ultrasonically vibrated. As a result, the fatty tissue that has adhered to the outer periphery of the blood vessel 59 is emulsified, fractured, and removed mainly by an edge portion between an inner peripheral surface of the treatment portion 32 and the proximal end surface 82. The emulsification and fracture can be sufficiently promoted by cavitation that occurs on the proximal end surface 82 of the treatment portion 32. Additionally, when a branch diverges from the blood vessel 59, the proximal end surface 82 of the treatment portion 32 is softly pressed against the branch to perform hemostasis, and then the branch is cut off.

In this manner, the ultrasonic treatment apparatus according to this reference embodiment can efficiently remove a fatty tissue that has adhered to an outer periphery of a blood vessel.

Figure 18:
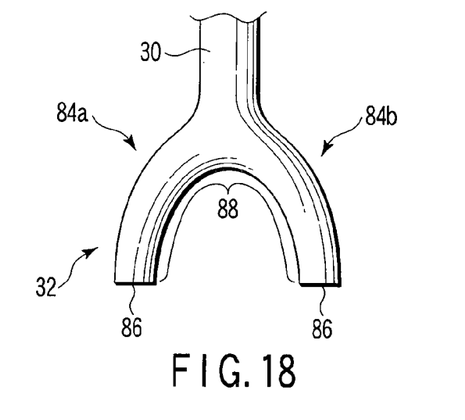
FIG. 18 is a top view showing a treatment portion according to a second reference embodiment of the present invention.
Figure 19:
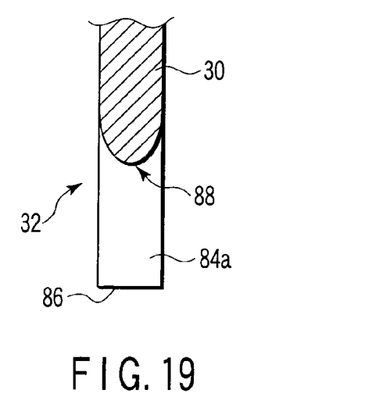
FIG. 19 is a side transparent view showing the treatment portion according to the second reference embodiment of the present invention.
Figure 20:
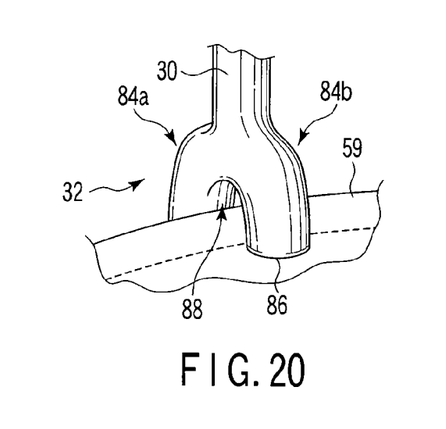
FIG. 20 is a perspective view showing a method for using the ultrasonic treatment apparatus according to the second reference embodiment of the present invention.

FIGS. 18 to 20 show a second reference embodiment according to the present invention.

Referring to FIGS. 18 and 19, a treatment portion 32 in an ultrasonic treatment apparatus according to this reference embodiment has a U-like forked shape, and is constituted of a first and a second extending portions 84a and 84b that extend toward a distal end side with curvature to be separated from a central axis of a probe 30. Distal end surfaces 86 perpendicular to the central axis direction of the probe 30 are respectively formed at distal ends of these first and second extending portions 84a and 84b. Each of these distal end surfaces 86 forms a shape with a large resistance coefficient, and facilitates cavitation. On the other hand, in the treatment portion 32, an inner side portion 88 of the U-like forked shape forms a shape with a small resistance coefficient, e.g., a streamline shape, and the inner side portion 88 suppresses cavitation.

Referring to FIG. 20, when using the ultrasonic treatment apparatus according to this reference embodiment to remove a fatty tissue covering a blood vessel 59, the blood vessel 59 buried in the fatty tissue is arranged between the first and the second extending portions 84a and 84b to become perpendicular to the extending direction of these extending portions 84a and 84b. Further, the treatment portion 32 is ultrasonically vibrated and moved forward/backward along an extending direction of the blood vessel 59 while swiveling the first and the second extending portions 84a and 84b around the blood vessel 59. As a result, the distal end surfaces 86 of the first and the second extending portions 84a and 84b emulsify, fracture, and remove the fatty tissue covering the blood vessel 59. At this time, cavitation produced by the distal end surfaces 86 of the first and the second extending portions 84a and 84b promotes emulsification and fracture and cavitation is suppressed on the inner surface portion 88 of the U-like forked shape so that an unnecessary treatment is not given to the exposed blood vessel 59.

As explained above, in the ultrasonic treatment apparatus according to this reference embodiment, a fatty tissue that covers a blood vessel can be efficiently emulsified, fractured, and removed, and an unnecessary treatment can be prevented from being given to the exposed blood vessel.

Figure 21:
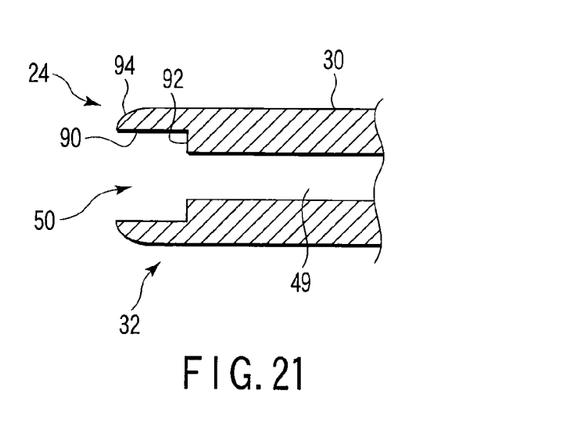
FIG. 21 is a longitudinal cross-sectional view showing a treatment portion according to a third reference embodiment of the present invention.

FIG. 21 shows a third reference embodiment according to the present invention.

Referring to FIG. 21, a treatment portion 32 of an ultrasonic aspirator 24 according to this reference embodiment has a substantially cylindrical shape. However, a large diameter portion 90 having a large internal diameter that allows a living tissue to be pulled in is formed at a distal end of an aspiration path 44. A step portion 92 is formed at a proximal end of this large diameter portion 90. This step portion 92 has a shape with a large resistance coefficient, and promotes cavitation. A distal end side outer peripheral surface 94 of the treatment portion 32 is formed into a shape with a small resistance coefficient, e.g., a streamline shape that is smoothly continuous from the distal end to the proximal end side, and suppresses cavitation.

In order to emulsify and fracture a fatty tissue by using the ultrasonic aspirator 24 according to this reference embodiment, the treatment portion 32 is ultrasonically vibrated and pressed against the fatty tissue while performing aspiration by the aspiration apparatus. As a result, the fatty tissue is pulled into the large diameter portion 90 at the distal end of the aspiration path 44, and the pulled fatty tissue is emulsified and fractured mainly by the step portion 92. At this time, cavitation produced by the step portion 92 promotes emulsification and fracture and cavitation is suppressed on the distal end outer peripheral surface of the treatment portion 32 so as to prevent unnecessary treatment from being given to, e.g., a blood vessel or a nerve in the fatty tissue.

As explained above, the ultrasonic aspirator 24 according to this reference embodiment can efficiently emulsify and fracture a fatty tissue, and prevent an unnecessary treatment from being given to, e.g., a blood vessel or a nerve in the fatty tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic treatment apparatus comprising:
an ultrasonic transducer configured to generate ultrasonic vibrations;
a probe including a proximal end connected with the ultrasonic transducer and configured to transmit the ultrasonic vibrations generated by the ultrasonic transducer from the proximal end to a distal end of the probe; and
a treatment portion formed at the distal end of the probe and configured to treat a living tissue with the transmitted ultrasonic vibrations,
wherein the treatment portion includes two or more protrusions,
the protrusion includes a promoting portion configured to promote cavitation, and
the promoting portion includes a hole portion.

2. A probe for an ultrasonic treatment apparatus, wherein the probe includes a proximal end configured to be connected with an ultrasonic transducer configured to generate ultrasonic vibrations; is configured to transmit the ultrasonic vibrations generated by the ultrasonic transducer from the proximal end to a distal end of the probe in an axial direction of the probe; and includes a treatment portion formed at the distal end of the probe and configured to treat a living tissue with the transmitted ultrasonic vibrations, the treatment portion includes two or more protrusions,
the protrusion includes a promoting portion configured to promote cavitation, and
the promoting portion includes a hole portion.

3. An ultrasonic treatment apparatus comprising:
an ultrasonic transducer configured to generate ultrasonic vibrations;
a probe including a proximal end connected with the ultrasonic transducer and configured to transmit the ultrasonic vibrations generated by the ultrasonic transducer from the proximal end to a distal end of the probe in an axial direction of the probe; and
a treatment portion formed at the distal end of the probe and configured to treat a living tissue with the transmitted ultrasonic vibrations, in a manner which produces cavitation,
wherein the treatment portion includes at least a first and a second protrusion,
the first protrusion is arranged on one side in a direction perpendicular to a central axis of the probe and is inclined to be separated from the central axis of the probe toward the distal end side,
the second protrusion is arranged on the opposite side to the first protrusion with respect to the central axis of the probe and is inclined to be separated from the central axis of the probe toward the distal end side,
the first protrusion includes a first main flat surface portion and the first main flat surface portion is flat, is arranged on a side of the first protrusion close to the second protrusion and is inclined to be separated from the central axis of the probe toward the distal end side, and
the second protrusion includes a second main flat surface portion and the second main flat surface portion is flat, is arranged on a side of the second protrusion close to the first protrusion, is inclined to be separated from the central axis of the probe toward the distal end side and faces the first main flat surface portion.

4. The ultrasonic treatment apparatus according to claim 3, wherein the treatment portion includes only the first protrusion and the second protrusion.

5. The ultrasonic treatment apparatus according to claim 3, wherein the treatment portion includes only the first protrusion, the second protrusion and a third protrusion,
the first protrusion is arranged on one side in a first direction perpendicular to the central axial direction of the probe and one side in a second direction perpendicular to the central axial direction of the probe and to the first direction with respect to the central axis of the probe and is inclined in the first direction toward the distal end side, and
the second protrusion is arranged on the other side in the first direction opposite to the first protrusion with respect to the central axis of the probe and is inclined in the first direction toward the distal end side,
the third protrusion is arranged on the one side in the first direction opposite to the second protrusion and on the other side in the second direction opposite to the first protrusion with respect to the central axis of the probe and is inclined to be separated from the central axis of the probe in the first direction toward the distal end side,
the first main surface portion is inclined in the first direction toward the distal end side,
the first protrusion includes a first sub flat surface portion and the first sub flat surface portion is flat and is arranged on a side of the first protrusion close to the third protrusion, the second main surface portion is inclined in the first direction toward the distal end side, and the third protrusion includes a third main flat surface portion and a third sub flat surface portion, the third main flat surface portion is flat, is arranged on a side of the third protrusion close to the second protrusion, is inclined to be separated from the central axis of the probe in the first direction toward the distal end side and faces the second main flat surface portion and the third sub flat surface portion is flat, is arranged on a side of the third protrusion close to the first protrusion and faces the first sub flat surface portion.

6. The ultrasonic treatment apparatus according to claim 3, wherein the treatment portion includes only the first protrusion, the second protrusion, a third protrusion and a fourth protrusion.

the first protrusion is arranged on one side in a first direction perpendicular to the central axial direction of the probe and one side in a second direction perpendicular to the central axial direction of the probe and to the first direction with respect to the central axis of the probe and is inclined in the first direction toward the distal end side, the second protrusion is arranged on the other side in the first direction opposite to the first protrusion with respect to the central axis of the probe and is inclined in the first direction toward the distal end side, the third protrusion is arranged on the one side in the first direction and on the other side in the second direction opposite to the first protrusion with respect to the central axis of the probe and is inclined to be separated from the central axis of the probe in the first direction toward the distal end side, the fourth protrusion is arranged on the other side in the first direction opposite to the third protrusion and on the other side in the second direction opposite to the second protrusion with respect to the central axis of the probe and is inclined to be separated from the central axis of the probe in the first direction toward the distal end side, the first main surface portion is inclined in the first direction toward the distal end side, the first protrusion includes a first sub flat surface portion and the first sub flat surface portion is flat, is arranged on a side of the first protrusion close to the third protrusion, the second main surface portion is inclined in the first direction toward the distal end side, the second protrusion includes a second sub flat surface portion and the second sub flat surface portion is flat, is arranged on a side of the second protrusion close to the fourth protrusion, the third protrusion includes a third main flat surface portion and a third sub flat surface portion, the third main flat surface portion is flat is arranged on a side of the third protrusion close to the fourth protrusion, is inclined to be separated from the central axis of the probe in the first direction toward the distal end side and the third sub flat surface portion is flat, is arranged on a side of the third protrusion close to the first protrusion and faces the first sub flat surface portion, and the fourth protrusion includes a fourth main flat surface portion and a fourth sub flat surface portion, the fourth main flat surface portion is flat, is arranged on a side of the fourth protrusion close to the third protrusion, is inclined to be separated from the central axis of the probe in the first direction toward the distal end side and faces the third main flat surface portion and the fourth sub flat surface portion is flat, is arranged on a side of the fourth protrusion close to the second protrusion and faces the second sub flat surface portion.

7. The ultrasonic treatment apparatus according to claim 3, wherein the first and the second protrusions are configured to arrange a living tissue between the first and the second protrusion such that the living tissue crosses a protruding direction of the protrusions and faces the main flat surface portions.

8. The ultrasonic treatment apparatus according to claim 3, wherein the probe further includes an aspiration path opened at the treatment portion and extending from the distal end to the proximal end of the probe.

9. The ultrasonic treatment apparatus according to claim 3, further comprising:
a sheath provided on the probe; and
jaw provided at a distal end of the sheath and configured to be opened and closed with respect to the treatment portion to hold a living tissue in cooperation with the treatment portion.

10. A probe for an ultrasonic apparatus,
wherein the probe includes a proximal end configured to be connected with an ultrasonic transducer configured to generate ultrasonic vibrations, is configured to transmit the ultrasonic vibrations generated by the ultrasonic transducer from the proximal end to a distal end of the probe in an axial direction of the probe, and includes a treatment portion formed at the distal end of the probe and configured to treat a living tissue with the transmitted ultrasonic vibrations, in a manner which produces cavitation, the treatment portion includes at least a first and a second protrusion, the first protrusion is arranged on one side in a direction perpendicular to a central axis of the probe and is inclined to be separated from the central axis of the probe toward the distal end side, the second protrusion is arranged on the opposite side to the first protrusion with respect to the central axis of the probe and is inclined to be separated from the central axis of the probe toward the distal end side, the first protrusion includes a first main flat surface portion and the first main flat surface portion is flat, is arranged on a side of the first protrusion close to the second protrusion and is inclined to be separated from the central axis of the probe toward the distal end side, and the second protrusion includes a second main flat surface portion and the second main flat surface portion is flat, is arranged on a side of the second protrusion close to the first protrusion, is inclined to be separated from the central axis of the probe toward the distal end side and faces the first main flat surface portion.

11. The probe according to claim 10,
wherein the treatment portion includes only the first protrusion and the second protrusion.

12. The probe according to claim 10,
wherein the treatment portion includes only the first protrusion, the second protrusion and a third protrusion,
the first protrusion is arranged on one side in a first direction perpendicular to the central axial direction of the probe and one side in a second direction perpendicular to the central axial direction of the probe and to the first direction with respect to the central axis of the probe and is inclined in the first direction toward the distal end side,
the second protrusion is arranged on the other side in the first direction opposite to the first protrusion with respect to the central axis of the probe and is inclined in the first direction toward the distal end side, the third protrusion is arranged on the one side in the first direction opposite to the second protrusion and on the other side in the second direction opposite to the first protrusion with respect to the central axis of the probe and is inclined to be separated from the central axis of the probe in the first direction toward the distal end side, the first main surface portion is inclined in the first direction toward the distal end side, the first protrusion includes a first sub flat surface portion and the first sub flat surface portion is flat and is arranged on a side of the first protrusion close to the third protrusion, the second main surface portion is inclined in the first direction toward the distal end side, and the third protrusion includes a third main flat surface portion and a third sub flat surface portion, the third main flat surface portion is flat, is arranged on a side of the third protrusion close to the second protrusion, is inclined to be separated from the central axis of the probe in the first direction toward the distal end side and faces the second main flat surface portion and the third sub flat surface portion is flat, is arranged on a side of the third protrusion close to the first protrusion and faces the first sub flat surface portion.

13. The probe according to claim 10, wherein the treatment portion includes only the first protrusion, the second protrusion, a third protrusion and a fourth protrusion, the first protrusion is arranged on one side in a first direction perpendicular to the central axial direction of the probe and one side in a second direction perpendicular to the central axial direction of the probe and to the first direction with respect to the central axis of the probe and is inclined in the first direction toward the distal end side, the second protrusion is arranged on the other side in the first direction opposite to the first protrusion with respect to the central axis of the probe and is inclined in the first direction toward the distal end side, the third protrusion is arranged on the one side in the first direction and on the other side in the second direction opposite to the first protrusion with respect to the central axis of the probe and is inclined to be separated from the central axis of the probe in the first direction toward the distal end side, the fourth protrusion is arranged on the other side in the first direction opposite to the third protrusion and on the other side in the second direction opposite to the second protrusion with respect to the central axis of the probe and is inclined to be separated from the central axis of the probe in the first direction toward the distal end side, the first main surface portion is inclined in the first direction toward the distal end side, the first protrusion includes a first sub flat surface portion and the first sub flat surface portion is flat, is arranged on a side of the first protrusion close to the third protrusion, the second main surface portion is inclined in the first direction toward the distal end side, the second protrusion includes a second sub flat surface portion and the second sub flat surface portion is flat, is arranged on a side of the second protrusion close to the fourth protrusion, the third protrusion includes a third main flat surface portion and a third sub flat surface portion, the third main flat surface portion is flat, is arranged on a side of the third protrusion close to the fourth protrusion, is inclined to be separated from the central axis of the probe in the first direction toward the distal end side and the third sub flat surface portion is flat, is arranged on a side of the third protrusion close to the first protrusion and faces the first sub flat surface portion, and the fourth protrusion includes a fourth main flat surface portion and a fourth sub flat surface portion, the fourth main flat surface portion is flat, is arranged on a side of the fourth protrusion close to the third protrusion, is inclined to be separated from the central axis of the probe in the first direction toward the distal end side and faces the third main flat surface portion and the fourth sub flat surface portion is flat, is arranged on a side of the fourth protrusion close to the second protrusion and faces the second sub flat surface portion.

14. The probe according to claim 10, wherein the first and the second protrusions are configured to arrange a living tissue between the first and the second protrusion such that the living tissue crosses a protruding direction of the protrusions and faces the main flat surface portions.

15. The probe according to claim 10, further comprising:

an aspiration path opened at the treatment portion and extending from the distal end to the proximal end of the probe.

* * * * *